(12) United States Patent
Chadwick et al.

(10) Patent No.: US 9,539,343 B2
(45) Date of Patent: *Jan. 10, 2017

(54) DELIVERY OF VIRAL AGENTS

(75) Inventors: James Chadwick, Glasgow (GB); Michael Mattey, Glasgow (GB)

(73) Assignee: FIXED PHAGE LIMITED, Glasgow (GB)

(*) Notice: Subject to any disclaimer, the term of this patent is extended or adjusted under 35 U.S.C. 154(b) by 182 days.

This patent is subject to a terminal disclaimer.

(21) Appl. No.: 14/127,429

(22) PCT Filed: Jun. 25, 2012

(86) PCT No.: PCT/EP2012/062270
§ 371 (c)(1),
(2), (4) Date: Mar. 26, 2014

(87) PCT Pub. No.: WO2012/175749
PCT Pub. Date: Dec. 27, 2012

(65) Prior Publication Data
US 2014/0208464 A1  Jul. 24, 2014

(30) Foreign Application Priority Data
Jun. 23, 2011 (GB) .................. 1110647.3

(51) Int. Cl.
| | |
|---|---|
| C12N 7/00 | (2006.01) |
| A61K 47/48 | (2006.01) |
| A61K 35/76 | (2015.01) |
| A61L 15/36 | (2006.01) |
| A61L 15/44 | (2006.01) |
| A61K 35/768 | (2015.01) |
| A01N 37/46 | (2006.01) |
| A01N 63/00 | (2006.01) |

(52) U.S. Cl.
CPC ......... *A61K 47/48776* (2013.01); *A01N 37/46* (2013.01); *A01N 63/00* (2013.01); *A23K 10/10* (2016.05); *A23K 10/18* (2016.05); *A23K 10/30* (2016.05); *A23K 50/70* (2016.05); *A23K 50/75* (2016.05); *A61K 35/76* (2013.01); *A61K 35/768* (2013.01); *A61L 15/36* (2013.01); *A61L 15/44* (2013.01); *A61L 2300/404* (2013.01); *A61L 2300/442* (2013.01); *C12N 2795/00032* (2013.01)

(58) Field of Classification Search
None
See application file for complete search history.

(56) References Cited

U.S. PATENT DOCUMENTS

| | | | |
|---|---|---|---|
| 4,828,999 A | 5/1989 | Jackson | |
| 2007/0222104 A1 | 9/2007 | Sukuzi | |
| 2015/0250897 A1* | 9/2015 | Mattey | ............... A01N 63/00 424/489 |

FOREIGN PATENT DOCUMENTS

| | | |
|---|---|---|
| DE | 10 2007 054127 | 5/2009 |
| JP | 2005-523943 | 8/2005 |
| WO | 03/093462 | 11/2003 |
| WO | 2005083165 | 9/2005 |
| WO | 2006/047872 | 5/2006 |
| WO | 2006/125319 | 11/2006 |

OTHER PUBLICATIONS

Xu et al. Bioluminescence imaging of Clavibacter *Michiganensis* subsp. *Michiganensis* infection of tomato seeds and plants. Appl Environ Microbiol. Jun. 2010;76(12):3978-88.*
Segonzac et al. Activation of plant pattern-recognition receptors by bacteria. Curr Opin Microbiol. Feb. 2011;14(1):54-61.*
Rakhuba et al. Bacteriophage receptors, mechanisms of phage adsorption and penetration into host cell. Pol J Microbiol. 2010;59(3)145-55.*
McKenna et al. Novel in vivo use of a polyvalent Streptomyces phage to disinfest Streptomyces scabies-infected seed potatoes. Plant Pathology (2001) 50, 666-675.*

* cited by examiner

*Primary Examiner* — Michelle S Horning
(74) *Attorney, Agent, or Firm* — Casimir Jones, SC

(57) ABSTRACT

Plant material has bacteriophage has been attached, wherein the bacteriophage retains infectivity. The plant material includes fruits, vegetables, leaves, stems, flowers, roots, tubers, seedlings and seeds. Plant diseases and animal diseases can be treated. A separate composition comprises a carrier selected from (i) a filament, (ii) a planar material, and (iii) particles and/or beads, and bacteriophage covalently attached thereto, wherein the bacteriophage retains infectivity, useful in treatment or prevention of bacterial infection in a deep wound.

11 Claims, 11 Drawing Sheets

DELIVERY OF VIRAL AGENTS

CROSS REFERENCE TO RELATED APPLICATIONS

The present application is a U.S. 371 National Stage Entry of pending International Patent Application No. PCT/EP2012/062270, international filing date Jun. 25, 2012, which claims priority to GB Patent Application No. 1110647.3, filed Jun. 25, 2011, the contents of which are incorporated by reference in their entireties.

FIELD OF THE INVENTION

The present invention relates to a means for the delivery of viral agents (such as bacteriophage or other viruses), in a sustainable viable state, and in various formats suitable for prevention and control of microbial infection, colonisation and/or contamination. A system is provided which may also act as a means to locate and deliver genetically modified viable viruses suitable for delivery of specific genes/proteins as therapy or immunisation. The invention can be applied to counteract microbial/bacterial growth and/or colonisation in virtually any situation in which microbial/bacterial contamination, colonisation or infection is present or likely to occur and where the sustained antimicrobial activity of viruses such as bacteriophages might be beneficial.

BACKGROUND TO THE INVENTION

It is now generally accepted that microbial/bacterial contamination or infection is a major factor influencing normal biological/physiological functions (such as healing or growth) and the rate of decomposition in many biological systems and processes. In wound healing, preventing wound infection is a vital aspect of wound care and recovery. Since all wounds are susceptible to infection, wound care best practise endeavours to take this into account. Typically wounds are cleaned to remove foreign debris that may harbour bacteria, and where tissues have suffered severe trauma, tissue repair is frequently assisted through suturing. In major surgical procedures such as hip replacement this involves repair of several tissue layers, followed by a sterile wound dressing of a type generally available. Typically a sterile wound dressing is applied to the skin surface to aid cleanliness and prevent infection.

Despite these precautions infection can become established through ingress of material during injury or inadvertently during various medical/surgical procedures. Furthermore problems of wound infection are not confined to deep wounds. Infection can transform relatively minor lesions into chronic wounds that increasingly pose major health care problems, particularly for the elderly, diabetic or infirm.

Over and above wound cleansing, various approaches have been adopted in an attempt to prevent the establishment of deep seated wound infections. Typically, antibiotics have been used systemically and locally or strong disinfecting chemicals have been used (in dental reconstruction for example) in an attempt to rid deep wounds of infectious bacteria. Unfortunately even the application of strong antimicrobial chemicals is frequently unsuccessful in preventing infection becoming established or recurring. In large part this may be due to the inability of the disinfecting agent to completely eradicate all problem bacteria. Additionally, as is well known, many bacteria are now resistant to antibiotics and their effectiveness becomes diluted over time.

There is therefore a need for more effective means to counteract bacterial infection and contamination. One approach has involved utilising bacteriophages (viruses that attack and destroy bacteria) and various groups have reported their successful application. Central problems associated with application of bacteriophages as a means of counteracting infection have been deriving an appropriate means of delivery whilst ensuring bacteriophages remain stable and viable long enough to exert their powerful antimicrobial effects.

Administration in liquid is not realistic or practical in many situations. The need is for a means of delivery that is generally suitable for application of bacteriophages as bactericidal agents and that has utility in many situations including wound care. Since bacteriophages are susceptible to degradation and desiccation, this should ideally also confer enhanced viability and stability.

Many conventional dressings employ a material which is designed to absorb excess fluid from within the wound; as such fluids are frequently rich in nutrients and are capable of supporting abundant bacterial growth. Since a surgical opening or the skin surface is rarely absolutely free of bacteria, the dressing or bandage material soon supports a growing bacterial population. Not only can the bacteria cause serious infection, but they may also release harmful toxins which lead to significant problems in terms of wound management. One solution is to routinely change the wound dressing or bandage, in order to prevent bacterial build-up, but this is not always desirable and/or practicable.

An alternative approach is to treat the dressing with an agent which is designed to limit microbial growth. However, many such agents can leach out of the dressing once in contact with wound exudates, so limiting the effectiveness of the dressing and indeed can be problematic with the active agent causing irritation or damage to surrounding tissue.

There is therefore a desire to provide antimicrobial dressings in which the antibacterial agent is not readily released from the dressing, or where the release of the agent would not be deleterious to the subject being treated.

WO 03/093462 discloses a method for immobilising viruses, such as bacteriophage, to a substrate, such that the viruses still retain infectivity.

It is amongst the objects of the present invention to provide a means to introduce bacteriophage into contaminated areas and environments so that the stability of bacteriophages is enhanced and their antimicrobial activity retained. This includes infected wounds, ranging from surface lesions to deep wound environments.

Separately, bacterial infections of plants can result in reduced germination, growth and/or yields. It is desirous to treat or prevent those infections, but approaches to doing so currently risk adversely affecting another factor influencing plant growth.

Another object of the invention is to address plant bacterial infections and provide plant material treated according to the invention and uses thereof.

SUMMARY OF THE INVENTION

In a first aspect, the present invention provides a device for providing live virus, such as a bacteriophage, to or within a desired location, such as to or within a wound, the device defined as a live virus carrier composite (LVCC) comprising live virus attached to a carrier substrate. Such a LVCC may be used in situations where it is advantageous that the biological action of the virus shall convey therapeutic or other anti-microbial benefits. Typically this will entail viruses retaining their biological properties, and in the case of bacteriophages, retaining their ability to target, infect and destroy bacterial cells. The viruses may be bacteriophages that target bacteria responsible for wound infections. In the invention they are attached to the surface of a carrier substrate material so that their biological properties are maintained within an infected or contaminated environment.

The carrier surface may be provided, for example, by a filamentous, planar (sheet) material (for example as strips) or by the surface of particles and/or beads, and which is sufficient to allow virus attachment and immobilisation such that virus viability is retained.

The LVCC's may be provided singly or in combinations within a deep wound or at another relevant site so that the beneficial properties of the attached live virus are provided and delivered as required. The carrier/substrate may be any material onto which virus may be immobilised while concurrently sustaining viability and retaining antimicrobial properties suitable for application as an LVCC.

A composition of the invention may comprise a carrier selected from (i) a filament, (ii) a planar material, and (iii) particles and/or beads, and bacteriophage covalently attached thereto, wherein the bacteriophage retains infectivity.

The carrier is suitably biodegradable and/or biocompatible. Separately it may be tissue compatible and able to be absorbed in situ.

A use of the composition lies in treatment or prevention of bacterial infection in a deep wound, by which is meant a wound that is not on an exposed surface of the body. A deep wound may be an internal wound, including an internal would closed by sutures on the body surface Typically, a composition of the invention is located in a deep wound which is then closed up. A filament of the invention can thus be located at and left in a deep wound. In an embodiment of the invention described in more detail below, location of a filament to which bacteriophage were attached in a deep wound resulted in a well healed wound compared to the control.

Advantageously the material of the composition is a biodegradable and/or biocompatible material, or make of a polymer or other material that is tissue compatible and can be absorbed in situ. Degradation can occur over time so that the anti-microbial action or other relevant property of the attached virus (such as bacteriophage) is not substantially affected.

In an embodiment of the invention, LVCC's are attached to various surgical implants such as prostheses, stents, catheters, membranes or scaffold material for surgical repair or to material utilised as scaffold or framework for regenerative purposes, suture anchors, sutures and other wound closure devices (for example adhesive strips or staples), shunts, catheters, in dwelling canulas, tubes and similar devices and components thereof etc. They may be attached onto the surface or incorporated into scaffold or supporting materials comprised of various non-biodegradable polymers, biodegradable polymers, collagen, keratin, cellulose, cotton, silk and other similar substances singly or in combination (see below).

The invention describes the construction of LVCC through immobilisation of viruses to the surface of a carrier substrate material so that their viability and biological properties (for bacteriophage this includes their bactericidal properties) are sustained and prolonged in hostile environments (such as infected or contaminated areas) that would quickly denature fee virus. Listed below are examples of materials that may be used singly or in combination or as mixtures or as co polymers and suitable for use as carrier substrates within an LVCC.

Suitable polymer classes include biopolymer, conductive polymer, copolymer, fluoropolymer, polyterpenes, phenolic resins, polyanhydrides, polyesters, polyolefins (polyalkenes), rubber, silicone, silicone rubber, superabsorbent polymers, synthetic rubbers, vinyl polymers, nucleic acids, polypeptides, sugars, polylactic acid (PLA poly-3-hydroxybutyrate, Inorganic polymers, homo-atomic polymers, polysilanes, polygermanes, polystannanes, hetero-atomic polymers, polyborazylenes, polysiloxanes, polydimethylsiloxane (PDMS), polymethylhydrosiloxane (PMHS) and polydiphenylsiloxane); polysilazanes like perhydridopolysilazane PHPS, polyphosphazenes, polythiazyls, polysulfides, ultra high molecular weight polyethylene (UHMWPE), common plastics, polypropylene polyester (PES), polyethylene terephthalate (PET), polyethylene (PE), high-density polyethylene, polyvinyl chloride (PVC), polyvinylidene chloride (PVDC) (Saran), low-density polyethylene (LDPE), polypropylene (PP), polystyrene (PS), high impact polystyrene (HIPS), polyamides (PA) (Nylons), acrylonitrile butadiene styrene (ABS), polycarbonate (PC), polycarbonate/acrylonitrile butadiene styrene (PC/ABS), polyurethanes (PU), special purpose plastics, monomers and polymers (including biodegradable/reabsorbale materials), ethylene methyl acrylate, melamine formaldehyde (MF), plastarch material, phenolics (PF) or (phenol formaldehydes), polycaprolactone (PCL), poly dioxanone (PDO or PDS), polyetheretherketone (PEEK), polyetherimide (PEI) (Ultem), polyglycolic acid (PGA), polyhydroxybutyrate (PHB), polylactic acid (PLA) D and L type stereoisomers, polylactide Poly-D-L-lactic acid copolymer polyglycolic acid (PDLLA-co-PGA), poly-L-lactic acid (PLLA), polymethyl methacrylate (PMMA), polytetrafluoroethylene (PTFE), poly-trimethylene carbonate (TMC), polycarbonates, poly-anhydrides, Poly-(imide anhydrides) and poly-orthoesters.

Other materials include urea-formaldehyde (UF), tricalcium phosphate (TCP), natural materials, wood, ceramics, rock, grit and stone; horn and keratin; bone; leather; paper; silk; cotton; hemp; glass, ferous and non-ferrous metals and metal alloys Specialist materials that can be used include processed cellulose as fibres or fabric (carboxymethylated), collagen, hyaluronic acid, hydro colloids, hydrogels, films, foams, alginates, ethyl methyl acrylate, specialist glasses (biodegradable and non-biodegradable), specialist nylons, polysaccharides, In another embodiment of the invention, viruses (for example bacteriophage) may be immobilised directly to the surfaces of the material comprising the device. In essence the material from which the device is formed becomes the LVCC carrier material. For example immobilising bacteriophage to surgical sutures at once provides an LVCC having dual purpose, capable of wound closure while delivering a potent antibacterial capability. Sutures may be of various types including biodegradable polymers.

In a further embodiment of the invention LVCC's (as filaments or strips to which bacteriophage have been attached singly or in combination) may be added to and/or beneath a wound dressing or used in conjunction with other types of dressing or device that may convey specific advantages, but that receive an enhanced antimicrobial function as a result of concurrent LVCC application.

A further embodiment of the present invention involves incorporation of the LVCC as part of a wound dressing. This may be as a separate (LVCC) component that is formatted to be an integral part of the dressing or distinct from it but introduced within and/or beneath the dressing to provide an antimicrobial function. Alternatively the carrier material may be part of the dressing. The LVCC or carrier material may be formatted in various ways, such as described below, but which are not to be construed as limiting.

A particular wound dressing of the invention comprises a plurality of filaments to which bacteriophage are attached, wherein there is at least a first filament to which a first bacteriophage is attached and a second filament to which a second bacteriophage is attached and wherein the first and second bacteriophage infect bacteria of different strains or species.

The first and second filaments can be of different colours. This provides colour coding of the dressing. Hence, in use, colours are used to identify the disease that is treatable or preventable by a given dressing, the colours being consistently to indicate which bacterial specificity is exhibited by the phage attached to that filament or part of the dressing. In a specific example, filaments of one colour have phage that infect *S. aureus* attached and filaments of a second colour have phage that infect *C. difficile* attached.

Typically a wound dressing or bandage comprises a dressing layer for providing wound protection and/or for absorbing wound fluid, and a wound contact surface, at least a portion of which may comprise viruses immobilised thereon.

The contact surface may be part of the dressing layer or may be part of a further component, such as part of a cover which surrounds or overlays the first material. In one embodiment, the contact surface may be permeable so as to allow fluid to pass through and ingress to the dressing layer. The wound contact surface is generally a portion of a material which may be placed in contact with the wound to be treated, although contact may not be direct. Thus, for example, a further permeable substrate may be positioned between the wound and the contact surface upon which the viruses are immobilised. In this manner wound fluid, which may comprise any microbial agent, is able to penetrate the permeable substrate and contact the immobilised virus present on the contact surface.

Indeed, the contact surface may incorporate an LVCC as a component designed to be inserted within a pouch or the like formed in a dressing. In this manner different inserts comprising different immobilised viruses may be provided and a desired insert chosen and placed within a dressing, depending on the type of wound being treated. Indeed a wound may be tested to ascertain which type of microbial agents may be present and an insert chosen appropriately to target such microbes. Alternatively LVCC's comprised of several bacteriophage providing a general broad spectrum antimicrobial action may be employed.

In one embodiment, a wound dressing might comprise three components: an outer covering for attaching the dressing to the skin for example, either through bandage or adhesive; a dressing middle layer that may act to buffer against knocks and abrasion and may also provide a function in aid of the healing process—an example might be absorbent lint, material that has been used in basic dressing formats for many years; and an inner membrane forming the contact surface which is in contact with the wound. This may comprise, for example, a synthetic polymer woven into a sheet or mesh and perhaps coated with a substance to ensure the dressing can easily be removed.

In a simple example of a dressing incorporating bacteriophage, phage may be attached to the surface of an inner layer (the contact surface), or that inner layer be introduced as a LVCC and distinct from the dressing, but which is brought into contact with a wound. General positioning serves to locate phage in the area where bacterial wound infection is/may become established and optimises the likelihood that an initial infectious bacteriophage event can occur, so initiating a cycle of ever amplifying bacterial destruction.

In one embodiment a dressing or LVCC may be devised to be active against a single type of bacterium and so would involve immobilisation of phage (or phages) active against a single type of bacteria.

Another embodiment may involve phages immobilised across the entire area of the contact surface. However, in some instances, this may prove unnecessary or not the most economical method for either immobilisation or manufacture. Other formats may be possible. For instance phages may only be attached to defined areas of a contact surface. This may be achieved through activation of only parts of the surface and an attachment process that allows phage access to the whole surface, but with immobilisation occurring only at an activated area. Alternatively phages may be directed into activated areas only, in a type of printing technique. This may require an arrangement (the reversal of the above) in which phage are activated prior to the attachment process and subsequently 'printed' onto a suitable surface. Alternatively both phage and surface may be activated either concurrently or in the case of dressings carrying multiple phage at different times—to provide an alternative method of manufacturing dressings carrying multiple phage types.

All the above may involve viruses/phages contained in a suitable buffer, which may or may not contain a dye for product identification or as an indicator to provide a signal that a dressing is due for change or not. Alternatively a dye as indicator might be utilised separately as a marker or to distinguish particular virus/phage attachment areas. A dye may also form a linker to attach virus/phage to certain surfaces.

Additionally virus/bacteriophage may be attached to specified areas and applied in various patterns so reducing the quantity of virus/phage required for manufacture. Moreover, patterning and/or colour markers may be used in LVCC or dressing identification. Further, viruses/phages may be attached to pre-coloured areas according to the type of virus/phage. Alternatively they might be attached to non-coloured areas.

In a variation of the above viruses/phage may be attached at the periphery of a dressing to discourage subsequent ingress of microbes, or a conventional antibacterial agent (disinfectant or antibiotic) might be used at the periphery. As such, phage may be applied to dressings or LVCC's either singly or in combination with antibacterial compounds (disinfectant, antibiotic or other) and/or enzymes, which may also be immobilised, for specific purposes to either augment the effects of attached phage, assist their action, for example by removing biofilms, or applied in conjunction with phage to provide an anti microbial barrier. In this manner, dressings and LVCC's may comprise more than one type of antimicrobial agent and may comprise several viruses/phages allied to several other agents be they conventional antimicrobial chemical agents or enzymes. Indeed, such combinations may work synergistically.

An alternative involves attaching phage to LVCC fibres or strands as described above, which may be coloured (also as described above) and can be attached to surfaces or interwoven within a surface, or both. Fibres may be woven or attached in various patterns to signify type of dressing or LVCC. The fibres may have phage attached before or after incorporation onto/into the active/contact surface Moreover, the LVCC fibres may be coloured according to phages employed or alternately may be colourless but woven into colour printed areas of a dressing contact surface or other area of the dressing.

Alternatively fibrous LVCC's may comprise two or more strands, coloured or non-coloured, and having virus/phage attached to one strand or both (as described below for multiple phage dressing options) and attached or perhaps fully integrated within a dressing.

Another option is to incorporate virus/phage into dressings through attachment to the middle dressing layer according to any of the above methods, so that access to target microbes occurs through a permeable or mesh membrane located adjacent to a wound.

An additional embodiment may involve incorporation of LVCC comprised of phage attached to particles and/or beads composed of various carrier substances. This may be achieved through attachment to particles/beads directly or immobilisation upon a sheet or planar surface that can be finely divided to generate many small particles, or fine strips. Particles may be administered through aerosol or nebulizer and may also be sprayed or printed on any dressing or LVCC or directly onto/into the area of need.

Additionally bacteriophage may be attached to various surfaces through a two stage activation process whereby phage are immobilised to a filament, particle or bead to generate an LVCC. In a second step the LVCC is itself immobilised/attached to the surface of a device such as those earlier described. Alternately material onto which phage can be immobilised may be irreversibly bound to a device (such as a prosthesis) followed by a second activation step which immobilises phage to the carrier substrate bound to the device.

The construction of an LVCC or dressing active against multiple microbes/bacteria is possible. One approach may involve utilising a heterogeneous mixture containing several different phage types that is used as a bulk phage source for immobilisation across an entire contact surface, or at specified locations as described above.

An alternative approach may involve specific phages held distinct and separate in homogeneous solutions that are activated and dispensed collaterally—a type of two (or multiple) jet printing. According to this embodiment, viruses/phages are activated and readied for immobilisation either prior to or concurrently as they move through the printing jet.

Another embodiment involves immobilising specific phage types in defined order on to the LVCC or dressing contact surface through several surface activation steps. This approach employs those binding sites that remain following the initial immobilisation process so that sequential activation and attachment steps do not affect phage previously immobilised.

Alternatively phages might be attached to specific areas of a dressing contact surface, individually or in combination according to the type of treatment needed, through sequential activation of specific areas. The areas may be colour coded.

Additionally specific viruses/phages may be attached to LVCC's composed of individual fibres or fine strips and attached or woven into dressing surfaces or attached to other devices, as described above. Fibres may have virus/phage already immobilised upon them or may be activated to receive virus/phage once incorporated or may simply receive activated phage.

Fibres may be colour coded according to the type of virus/phages and then twisted into strands comprised of two or more filaments (similar to a barbers pole) that may then be woven or attached (or both) to the dressing or contact surface. Moreover, coloured indicator strips could be added (attached, woven or printed) that change colour over time to indicate optimum timing for dressing change.

Rather than incorporating fibres or strips all the above might be achieved through incorporation or attachment to dressing surfaces 'patches' of planar LVCC material (in various shapes) that may have viruses/phages attached or that are in place to allow attachment and may itself comprise of interwoven fibres or a combination of both.

The contact surface, fibres or strips may comprise indicators, such as a colour marker or the like, so to inform a user of the type of virus attached and/or to aid with correct positioning of the LVCC or dressing.

The immobilised viruses themselves may be modified such that they are capable of expressing a marker protein, such as green fluorescent protein or similar, such that when microbes are infected with the virus, the marker gene will be expressed and the marker protein produced. This in turn may be detected and the medical practitioner is alerted to the fact that microbes are present in the wound. The practitioner may then change the dressing at the appropriate time so as to retain an active bacteriophage population at the contaminated site, and keep doing this until no colour change is observed indicating the wound is therefore free of microbes. To facilitate this, the dressing may desirably be transparent or partially transparent so colouration at the wound surface can be observed.

The wound may be an internal wound or a wound involving several tissue layers or within the skin layers or at a subjects skin surface. Many types of wound are known, including those caused by trauma, surgery, burns, cuts, abrasions, ulcers, pressure sores and other lesions caused by diabetes, poor circulation and the like. The term is also used very broadly to encompass other applications where it may be desirable to absorb bodily fluids and prevent any serious microbial infection from occurring; one such application may be in women's hygiene products, such as tampons for absorbing menses and at the same time preventing or minimising development of toxic shock syndrome. It may also include actual surgical sites and hence immobilised phage would convey antimicrobial properties to absorbent materials which are often placed within a surgical area to absorb excess fluid or to barrier materials such as disposable products.

The subject may be any animal subject such as a domestic or farm animal, but may particularly be a human.

One embodiment of the present invention is to provide an absorbent medical or hygiene product that comprises an absorbent material having immobilised viruses attached to or within the absorbent material or to at least a portion of a permeable surface covering of the absorbent material. Such products include sanitary pads and tampons, nappies, sponges, sanitary wipes etc. The absorbent material described above and elsewhere may be natural or synthetic product comprising cellulose or cotton, a hyrdrogel polymer, carboxymethylcellulose, or any other suitable material.

In another embodiment LVCC's may be used to aid the storage, packaging and transport of materials and products susceptible to microbial degradation. This may be through inclusion in media or packaging or to assist and promote storage of materials and products. Such materials might include organs and other tissue or material that is destined for transplantation. An example might be corneal transplants that are stored and transported prior to use and which are susceptible to microbial contamination and degradation rendering the tissue unusable.

In another embodiment LVCC's are applied to a wide range of plant material, including fruits, vegetables, leaves, stems, flowers, roots, tubers, seedlings and seeds to be used for consumption or as stored seed stock. In accordance with embodiments of the invention, bacteriophage are immobilised directly to the surface of seeds so that the seed remains viable while its surface in effect becomes the carrier component of the LVCC, so providing a means to combat bacterial plant diseases occurring during storage, germination, harvest, and transportation and sale.

The invention hence provides plant material to which bacteriophage has been attached, wherein the bacteriophage retains infectivity.

A plurality of bacteriophage that infect different bacteria may be attached, giving a broader spectrum of activity.

Suitable plant material includes fruits, vegetables, leaves, stems, flowers, roots, tubers, seedlings and seeds. Seeds for consumption, e.g. by animals or birds are one example. Seed stock, e.g. being stored prior to being sowed, is another.

Plant material of the invention may be used for prevention or treatment of a plant disease or a disease in a creature that eats the plant material, such as bacterial infections in the gastrointestinal tract.

An example of a composition of the invention is animal or bird food comprising plant material of the invention, in particular seeds. The food can be in the form of a cake or pellet made from or comprising seed of the invention. The food can be in the form of a cake or pellet which is then treated to attach phage, such as by treating the food with an aqueous preparation of particles to which phage are covalently attached, then typically drying the food to attach the particles. Alternatively, a dry preparation of the particles can be combined with the food.

In general, the bacteriophage may be indirectly attached to the plant material, e.g. attached to a particle or particles which provide a method of delivering phage e.g. to counteract plant disease. For example, a solution of particles with phage attached can be sprayed onto and dried to stick them to the plant material. In an example below, such particles were attached to potato tubers by that sort of method. The phage retained viability and were effective in preventing disease of the tubers.

Hence, the invention includes methods comprising bringing an aqueous preparation of particles to which bacteriophage are covalently attached into combination with plant material and drying the combination to attach the particles to the plant material. Alternatively, a dry preparation of the particles can be combined with plant material, e.g. dusted onto the plant material.

In a specific embodiment of the invention described in more detail below, bacteriophage were covalently attached to tomato seeds. Tests in a separate embodiment confirmed that phage attached in this way to cellulose (such as found on the tomato seed surface) retained phage viability. Tomato seeds were used as an example. Other seeds can be used with similar results, from small (*Nicotiana*) to large (maize) seeds. Chemical and corona activation of seeds results in transient modification of the seed coat surface, which contains polymers related to cellulose or pectin with variable amounts of proteins and fatty acids. All such materials will, when exposed to a corona field, give rise to reactive free radical species, which will react with the protein coat of a bacteriophage or other entity and decay to give stable covalent bonds within seconds. The results showed that the corona activation was a surface phenomenon and viability of the seeds, as tested by germination, was not adversely affected—in fact germination was improved compared with no corona treatment.

Similar effects are seen when other plant materials (e.g. leaves, stems, flowers, roots) are treated in a corona field; the activation and reactions occur at the cuticle surfaces and results in bacteriophage attachment; damage to the plant only occurs if sparking between a tip of plant material and the corona electrode occurs. Hence plant material can have phage directly attached, e.g. covalently. Plant material can also be associated with or combined with particles to which phage are covalently attached. Particles bearing phage can be dried onto the plant material. The particles can otherwise be associated with the plant material.

In a further specific embodiment of the invention, potato tubers were treated with immobilised phage. In detail, phage was attached to the surface of cellulose particles and these were immobilised onto the potato surface by spraying the tubers with a solution of the particles and then drying the tubers—to enable the particles to adhere. Growth of the potato plants was surprisingly improved followed this treatment: incidence of infection was reduced, and also growth of the treated plants was significantly better.

In an embodiment the seed based form of LVCC may be used to deliver bacteriophage for treatment of seed eating creatures susceptible to bacterial infections such as those of the gastrointestinal tract. Similarly LVCC may be applied to other food stuffs for treatment of digestive and other diseases. Alternatively an LVCC can substitute for grit and so be utilised for treatment of Avian diseases. In this way bacteriophage counteracting bacterial pathogens can be administered into the gut for treatment of bacterial diseases of animals.

LVCC's may also be administered rectally for delivery of antibacterial treatment to the lower alimentary tract.

In yet another embodiment an LVCC may be used to deliver systemic bacteriophage therapy of animals through injection into the circulatory system or lymphatic system or directly into cerebrospinal fluid or other body cavities or organs where this may be desirable, for example to provide an antibacterial action. Alternatively LVCC's may allow delivery of bacteriophage or other viruses through inhalation to counter infections of the respiratory tract.

Immobilised is understood to relate to a specific physical immobilisation, such as by any chemical bonding (covalent, ionic, hydrogen or van der Waals bonding) and is therefore distinguished from any passive protuberance of the virus to a substrate. Moreover, immobilisation is such that the virus retains an ability to infect a cell or cells. Thus, immobilisation may occur through a head or capsid protein, or indeed any other surface protein of the virus, providing that the virus is still able to infect the desired target cell. More preferably, bacteriophage/virus are immobilised to the substrate via their head groups or nucleocapsid by activating the substrate before the addition and coupling of bacteriophage/virus. Covalent attachment is a preferred means of attachment.

The term "virus" according to the present invention includes double-stranded or single-stranded RNA or DNA viruses, including those that infect bacteria and are generally termed bacteriophage. In preferred embodiments the viruses are bacteriophages.

Many different types of bacteriophage/viruses are known in the art and suitable bacteriophage/viruses may be chosen depending on the bacterial problem to be addressed For example for wound treatment the clinician is likely to be aware of the common types of bacteria/protozoa/fungi which are likely to infect particular wounds and the wound dressing may comprise one or more different types of bacteriophage/viruses which are designed to infect and hence minimise growth of bacteria/protoza/fungi which may infect a particular wound.

Examples of potential wound pathogens include Streptococci, such as *Streptococcus pyogenes*; enterococci, such as *Enterococcus faecalis*; Staphylococci, such as *Staphylococcus aureus*, especially methicillin-resistant *Staphylococcus aureus* (MRSA); *Pseudomonas aeruginosa; Enterobacter* species; *Escherichia coli; Klebsiella* species; *Proteus* species; *Bacteroides; Clostridium*; yeasts such as candida; and *Aspergillus*.

The term "carrier/substrate" according to the present invention is understood to mean any solid phase material to which a virus may be immobilised. For example, said carrier may be a material which may be advantageously activated to allow, for example, head-group specific binding of a virus, such as complex bacteriophage. Said substrate may take many forms, for example, nylon and any other similar polymers, polymers with reactive groups, such as amino or carboxyl surface groups, cellulose or other hydroxyl-containing polymer, polystyrene or other similar polymer. Substrate may also comprise polymers as long chain macromolecules composed of multiple covalently bonded monomer subunits and composed of single repeating monomers or combinations of types of monomer. Typically they include natural, synthetic or biosynthetic bioabsorbable/bioresorbable material in monomeric or polymeric form, singly or in combination or as copolymers, such as polyglycolic acid (PGA) polylactic acid enenatiomers (PLA), and poly D-L-lactic acid copolymer polyglycolicacid (PDLLA-co-PGA), poly dioxanone (PDO) and polytrimethylene carbonate (TMC), polyetheretherketone (PEEK) and combinations and composites thereof. Substrates may also include plastics or other aforementioned polymers or beads or particles, which may be magnetic or comprised of biological material such as alginates, glasses or glass fibre, stainless steel, silicone, silk, collagen, or a ceramic material. More preferably, said substrate is made of a material commonly used in medical devices in treatment, or in support of treatments. For example, materials commonly utilised as sutures, and also lint or gauze material used to dress open wounds. In certain embodiments, the substrate may be biodegradable/bioreabsorbable and hence may degrade and be reabsorbed in vivo over time, when placed in contact with body fluids. The dressing layer may for example be formed of a hydrogel material to which the viruses are attached, which may also serve to absorb fluid from the wound and bring such fluid into contact with the immobilised viruses.

The term "activated/activating/activation" according to the present invention is understood to mean the activation of a substrate and/or virus by reacting said substrate/virus with various chemical groups (leaving a surface chemistry able to bind viruses, such as bacteriophage head or capsid surface proteins or groups). Alternatively, immobilisation may be achieved through electrical activation or other electrical discharge, field or field effects such as plasmas, microwaves, photo electric effects, radiofrequency field effects, gamma and other energetic radiation etc. This may be applied to the carrier substrate, or virus or both substrate and virus.

Activation of substrates may also be achieved by, for example, preliminary hydrolysis with an acid, preferably HCl followed by a wash step of water and an alkali to remove the acid. Preferably, said alkali is sodium bicarbonate. Binding of viruses, for example bacteriophage, via their head groups is important. In the case of complex bacteriophage for example, binding via head groups leaves the tail groups, which are necessary for bacteria-specific recognition, free to infect, i.e., bind and penetrate a host bacterial cell. It will be understood that this mechanism of infection of a host cell is similar for many other viruses other than viruses that infect and multiply only in bacteria. A plurality of viruses, e.g., various strain-specific bacteriophage, may be immobilised to a substrate at any one time.

Coupling of viruses to a substrate is as a result of the formation of bonds, such as covalent bonds between a viral coat protein and the substrate such as through an amino group on a peptide, for example a peptide bond. "Coupling Agents" that aid this process vary, dependent on the substrate used. For example, for coupling to the substrate nylon or other polymer with amino or carboxy surface groups the coupling agents carbodiimide or glutaraldehyde may be used.

For coupling to the substrate cellulose or other hydroxyl-containing polymer the coupling agents vinylsulfonylethylene ether or triazine may be used. Coupling agents for the coupling of virus to the substrate polythene or other similar polymer or many other polymer types, include corona discharge or permanganate oxidation.

Using corona discharge techniques it has been demonstrated that it is possible to immobilise virus to a wide range of substrates such that viral antimicrobial activity is sustained for extended periods under environmental conditions that would de-nature free virus. A comprehensive listing is given hereinabove and includes such substrates as: Nylon and related polymers, Dacron, Polystyrene, Plastics and related polymers, Natural and synthetic Rubbers, Bioabsorbable/Bioresorbable monomers, polymers, and copolymers either singly or in combination or as copolymers, such as polyglycolic acid (PGA) polylactic acid enenatiomers (PLA), and poly D-L-lactic acid copolymer polyglycolicacid (PDLLA-co-PGA), poly dioxanone (PDO) and polytrimethylene carbonate (TMC), polyetheretherketone (PEEK) and combinations and composites thereof, Silicon, Ceramics, Glasses and glass fibre, Metals including Steels, aluminium and metal alloys, Collagen, Keratin, Acrylics and various coatings, bone, Silk, Cellulose—including paper, cotton, lint, tapes, and gauzes, Rayon, Natural and synthetic sponges, Alginates, Hyaluronic Acid, Gel surfaces—such as hydrogels.

Generally speaking, coupling agents for the coupling of bacteriophage to a substrate include: S-Acetylmercaptosuccinic anhydride; S-Acetylthioglycolic acid N-hydroxysuccinimide ester; Adipic acid dihydrazide; 4-Azidobenzoic acid N-hydroxysuccinimide ester; N-(5-Azido-2-nitrobenzyloxy) succinimide; 6-(4~Azido-2-nitrophenylamino) hexanoic acid N-hydroxysuccinimide ester; p-Azidophenacyl bromide; 4-Azidosalicylic acid N-hydroxysuccinimide ester; Bromoacetic acid N-hydroxysuccinimide ester; 1,4-Butanediol diglycidyl ether; 2-Diazo-3, 3,3-trifluoroproprionic acid p-nitrophenyl ester; Diethyl malonimidate; 4,4'Diisothiocyanatostilbene-2,2'-disulfonic acid; Dimethyl adipimidate; Dimethyl 3,3'-dithiobispropionimidate; Dimethyl pimelimidate; Dimethyl suberimidate; 4,4'-Dithiobisphenyl azide; Dithiobis (propionic acid N-hydroxysuccinimide ester); Ethylene Glycol bis-(succinic acid N-hydroxysuccinimide ester); 4-Fluoro-3-nitrophenyl azide; p-Formylbenzoic acid N-hydroxysuccinimide ester; Glutaraldehyde; 2-Iminothiolane; 6-(Iodoacetamide) caproic acid N-hydroxysuccinimide ester; Iodoacetic acid N-hydroxysuccinimide ester; 3-Maleimidoacetic acid N-hydroxysuccinimide ester; 3-Maleimidobenzoic acid N-hydroxysuccinimide ester; 4-(N. Maleimido) benzophenone; y-Maleimidobutyric acid N-hydroxysuccinimide. ester; s-Maleimidocaproic acid N-hydroxysuccinimide ester; 4-(N-Maleimidomethyl)cyclohexenecarboxylic acid N-hydroxysuccinimide ester; 4-(N-Maleimidomethyl)cyclohexanecarboxylic acid 3-sulfo-N-hydroxysuccinimide ester; -Maleimidopropionic acid N-hydroxysuccinimide ester; N,N'-bis(3-Maleimidopropionyl)-2-hydroxy-1,3-propanediamine; 1,4-Phenylene diisothiocyanete; N,N'-o-Phenylenedimaleimide; Polyoxyethylene bis(glycidyl ether); bis(Polyoxyethylene bis(glycidyl ether); Polyoxyethylene bis(imidazolylcarbonyl) 1; Bis(Polyoxyethylene bis [Imidolylcarbonyl]); Polyoxyethylene bis(p-nitropheny) carbonate); 3-(2-Pyridyldithio) propionic acid N-hydroxysuccinimide ester; Suberic acid bis(N-hydroxysuccinimide) ester; Succinic Acid Maleimidoethyl-N-hydroxysuccinimideester; 1,5-bis(succinimidooxycarbonyloxy)-pentene; bis(N-succinimidyl) carbonate.

Advantageously, when virus is immobilised to a carrier substrate, said immobilization may confer stability. For example, the immobilised virus is stabilised in such a way that it maintains its viability and infectivity even when in contact with agents, for example proteases, which may otherwise quickly inactivate the virus. Similarly, when exposed to physical stress, such as dehydration, temperature or pH which would otherwise inactivate the virus.

The present invention will now be further described by way of example and with reference to the figures in which.

EXAMPLES

Example 1

Figure 1:
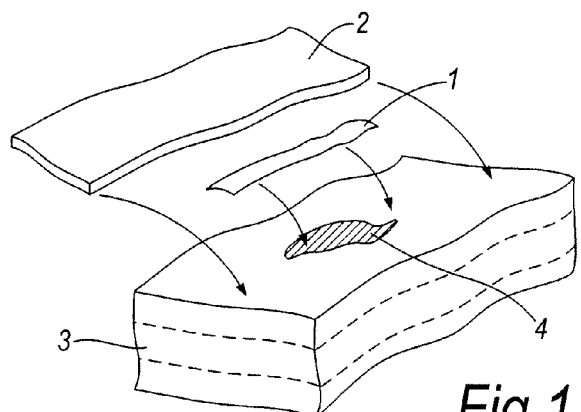
FIG. 1 shows a schematic diagram of a wound dressing to which an LVCC (as one or more filaments or strips to which bacteriophage have been attached singly or in combination) is added.

Effectiveness of LVCC for Delivery of Bacteriophage to Counteract Deep Wound Infection FIG. 1 shows schematically an LVCC of the invention (1) pressed onto a wound (4) in a tissue (3) by dressing (2).

Figure 2A:
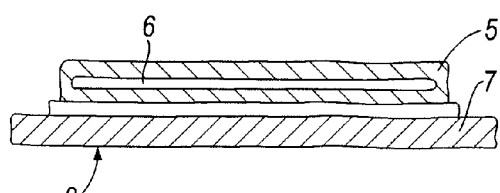
FIGS. 2a and 2b shows schematic diagrams of a dressing incorporating a LVCC.

FIG. 2a is an inverted dressing of the invention incorporating an LVCC, shown in cross section. A pouch (5) encloses an LVCC (6) adhered to dressing (7), having top dressing surface (8)—hence it is inverted in the figure.

Figure 2B:
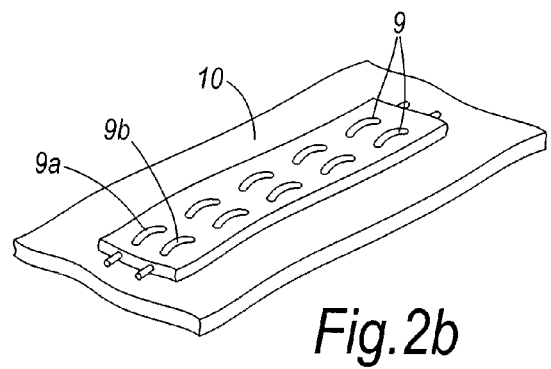
Figure 3:
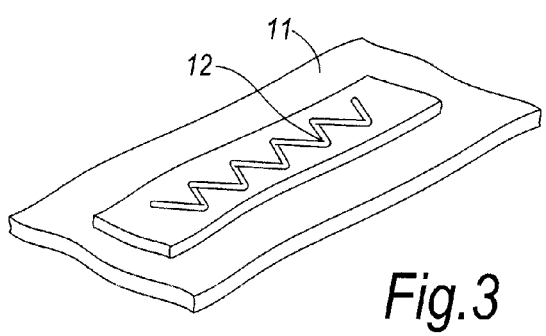
FIG. 3 shows a schematic diagram of a dressing bearing multiple bacteriophage in an identifiable pattern.

FIG. 2b shows schematically an LVCC (9) woven into a dressing (10). The two filaments (9a and 9b) are of different colours and have different bacteriophage attached. FIG. 3 shows a further schematic of a dressing (11) into which a filament with phage attached (12) is incorporated.

In a first example the effectiveness of an LVCC for delivering bacteriophage, to counteract bacterial infection within an infected deep wound environment using an in vivo model is demonstrated. Deep wounds penetrating several tissue layers and infected at all levels with Methycillin Resistant *Staphylococcus aureus* (MRSA) (E15) were treated with an LVCC comprised of bacteriophages active against the infecting MRSA strains.

Bacteriophage were immobilised to a synthetic nylon polymer filament similar to that used in the manufacture of wound closure sutures. Infected wounds were closed using the LVCC as suture, at various levels. The filamentous LVCC had either anti-MRSA bacteriophages immobilised to their surface (the prototype LVCC to be tested) or did not (control).

Figure 4A:
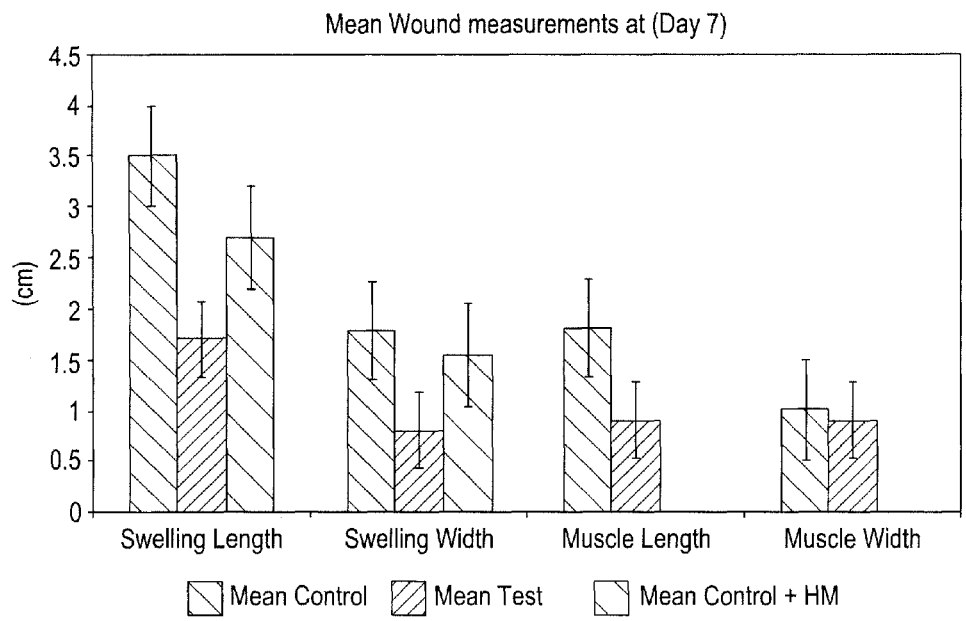
FIG. 4a shows wound statistics for animals with deep wound infected with 70 µl of 1×10⁵ cfu/ml E15 suspended in 5% hog gastric mucin using normal or bacteriophage treated LVCC-7 days post surgery.
Figure 4B:
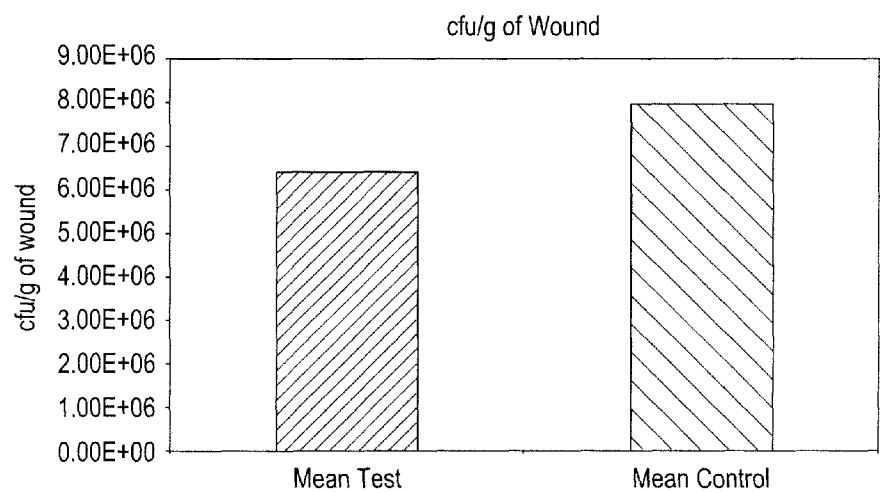
FIG. 4b shows bacterial load for animals with deep wound infected with 70 µl of 1×10⁵ cfu/ml E15 suspended in 5% hog gastric mucin using normal or bacteriophage treated LVCC-7 days post surgery.

In all subjects treated with the LVCC, infection was controlled and decreased (as demonstrated visually and by bacterial count (see FIGS. 4a and 4b) with wound healing proceeding normally. By contrast MRSA growth in control subjects proceeded unchecked resulting in an inflamed suppurating wound that did not heal.

The results show that, using LVCC's, bacteriophages can deliver a potent bactericidal effect for an extended period in an in vivo model—see Tables 1A and 1B.

Example 2

Extended Stability

LVCC's recovered from infected subjects were washed and stored at 4° C. and periodically evaluated for continuing antimicrobial activity against MRSA grown in vitro. In a series of experiments anti-MRSA activity was maintained as demonstrated by LVCC placed within a lawn of bacteria.

Figure 5:
FIG. 5 shows clearing of MRSA by bacteriophage immobilised onto sutures recovered from rats 14 days after insertion into infected wounds.

Bacteriophage activity (as shown by the clearing seen around the recovered LVCCs) extended several weeks following storage—see FIG. 5.

Example 3

Figure 6A:
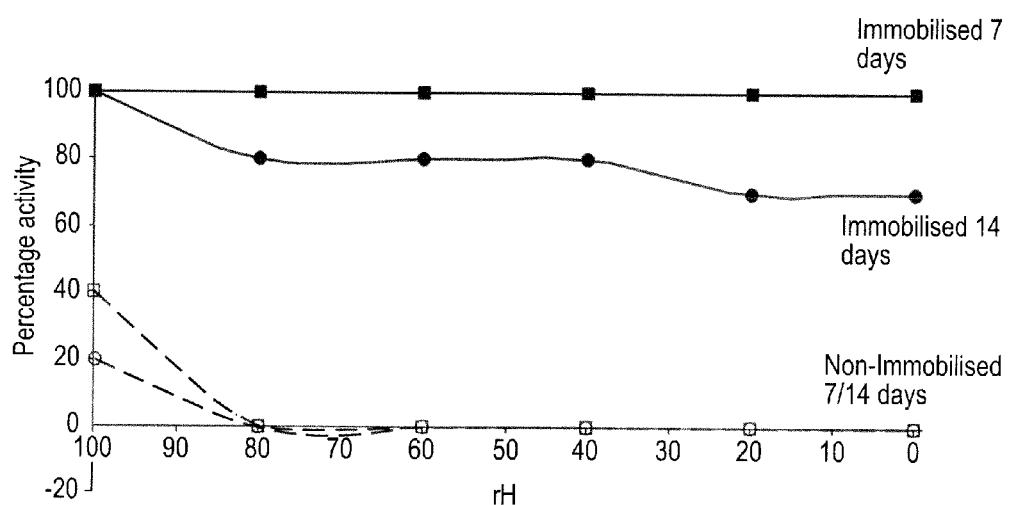
FIG. 6a shows stability conferred by LVCC against desiccation.
Figure 6B:
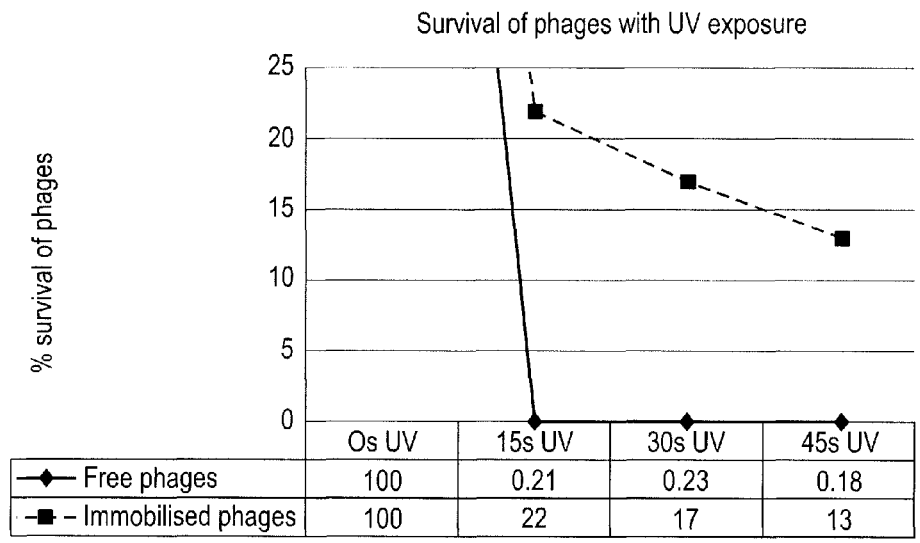
FIG. 6b shows stability conferred by LVCC against ultra violet radiation.
Figure 6C:
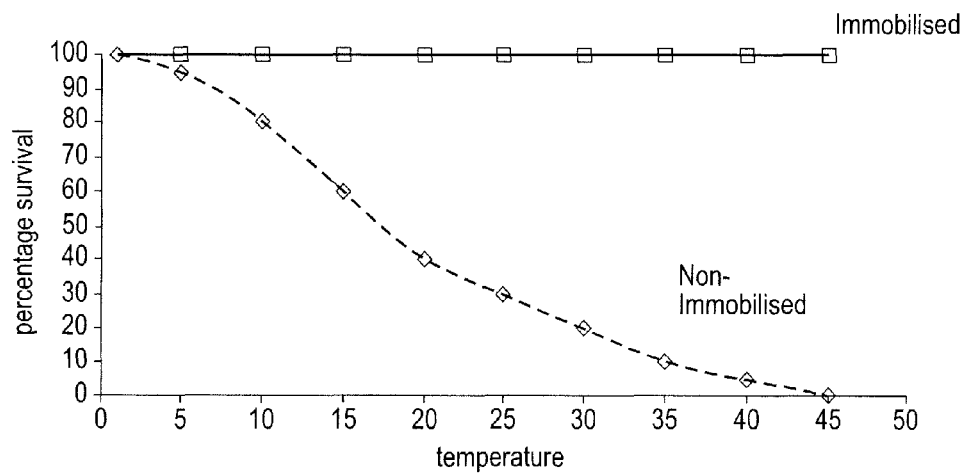
FIG. 6c shows stability conferred by LVCC against temperature.

Stability Conferred by LVCC Against Desiccation, Ultra Violet Radiation and Temperature In these examples LVCC were generated using activated nylon polymer or cotton fibres as the carrier substrate. LVCC with attached bacteriophage were exposed to a series of environmental conditions, including dehydration, shown by the effect of relative humidity on bacteriophage survival (see FIG. 6a), ultraviolet light (see FIG. 6b) and elevated temperature (see FIG. 6c), all conditions known to denature free bacteriophages.

Three 2×1 cm phage strips were placed on LBM agar and exposed to UV light in the sterile cabinet for 5, 15 and 30 min. The strips were then turned over and placed on a fresh area of agar and the UV exposure repeated. Control phage strips were treated similarly, but were shielded from UV. The strips were then transferred to 15 ml LB broth, inoculated with 50 ul Staphylococcus aureus suspension and incubated. Results—see Table 2

Conclusion: Attached phage can withstand up to 30 min exposure to cabinet UV. *S. aureus* bacterial cells are killed by 5 minutes exposure to the UV source.

Example 4

Sustained Viability in Extreme Environments

In this example the enhanced stability and viability of LVCC bacteriophage was determined following exposure to the astringent conditions provided by soil. The study involved construction of two types of LVCC using bacteriophage immobilised to either a nylon polymer or cellulose. Each LVCC was then buried in non sterilised or sterilised soil and samples taken over a three week period to assess the antibacterial activity of the LVCC.

Figure 7:
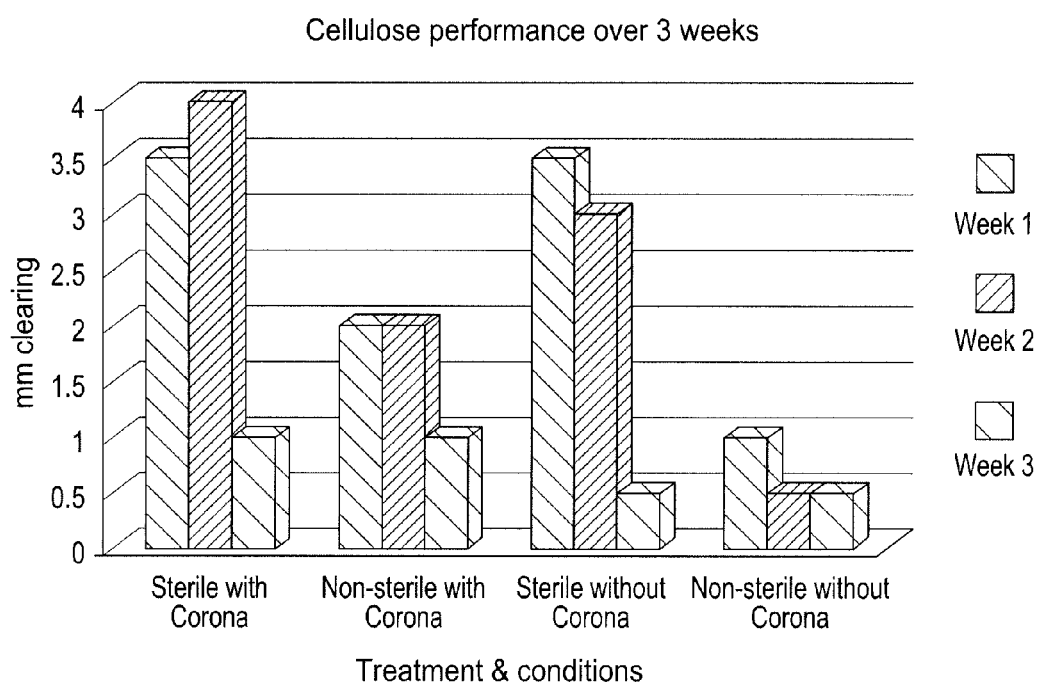
FIG. 7 shows survival of immobilised bacteriophages in soil.

Results show enhanced survival of bacteriophage for both LVCC bacteriophage types compared to free bacteriophage (see FIG. 7).

Example 5

LVCC Composed of Multiple Bacteriophage

Evaluation of LVCC performance using two bacteriophages active against two different target bacteria following immobilisation onto a common carrier substrate and tested for antibacterial activity. Percentage clearing on bacterial lawn is based upon the average clearing by each phage on their host strain measured in mm).

Figure 8:
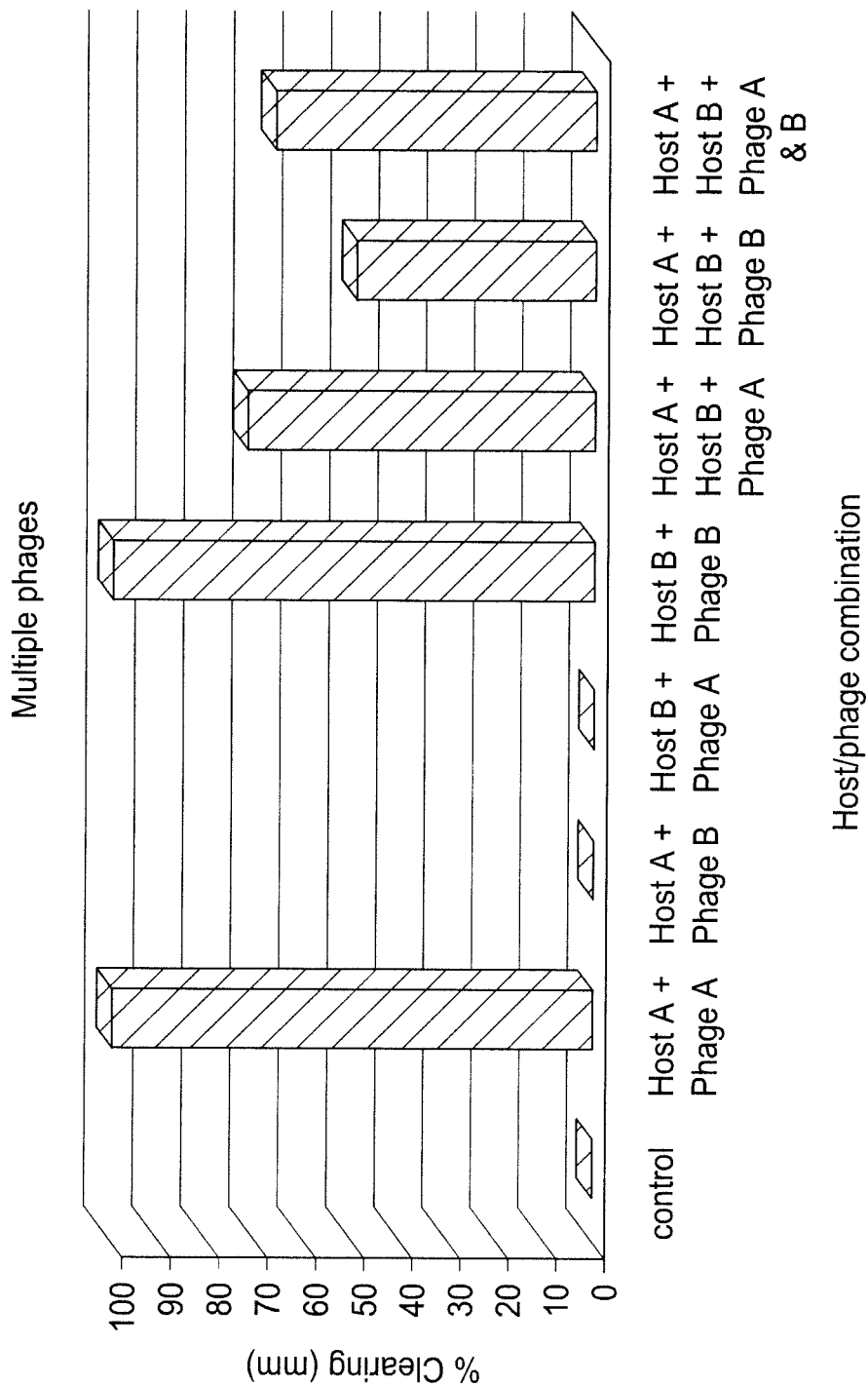
FIG. 8 shows exposure of LVCC with two bacteriophages to two bacterial species each susceptible to one of the bacteriophages.

Results show no diminution in antibacterial activity, with LVCC bacteriophages remaining active against both target bacteria (see FIG. 8). Exposure of treated material to 2 bacterial species (1 host, 1 non-host) still results in clearing of susceptible hosts.

Example 6

Deep Wound Treatment

In 10 control animals (rats), a deep incision into the paraspinous muscle was infected with 100 μl of 5×10$^7$ cfu/ml E15 MRSA suspended in 5% hog gastric mucin and the wound was closed with normal sutures. The 10 test animals with the same incision received 100 μl of 5×10$^7$ cfu/ml E15 MRSA suspended in 5% hog gastric mucin and a bacteriophage treated filament was inserted into the deep wound. The bacteriophage immobilised was phage K.

All animals were treated with analgesics following surgery and observed at hourly intervals for the first 12 hours and at 3 hour intervals for the next 12 hours, then at 6 hourly intervals for the next 2 days post infection and twice daily thereafter.

Wound sites were examined at these time intervals for signs of inflammation and infection (pus formation) up to 14 days. Visual results are presented in Table 3.

Figure 9:
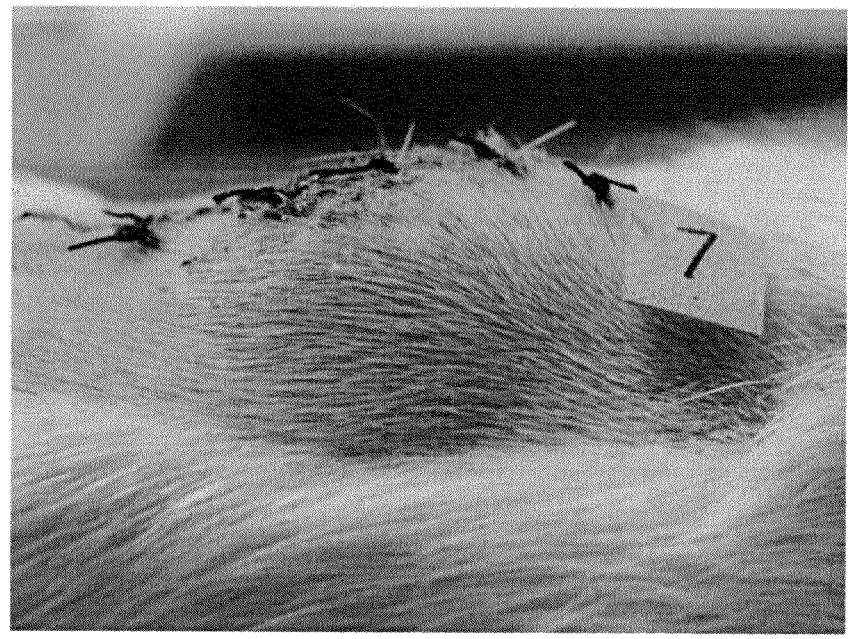
FIG. 9 shows a lateral, external view of an infected control would site on day 14.
Figure 10:
FIG. 10 shows a dorsal, internal view of an infected control would site on day 14.

Referring to FIG. 9, showing the infected control: as seen, the site remained large and swollen and was poorly if at all healed, with a raised incision site on day 14. When opened, as shown in FIG. 10, a pus-filled incision site was revealed.

Figure 11:
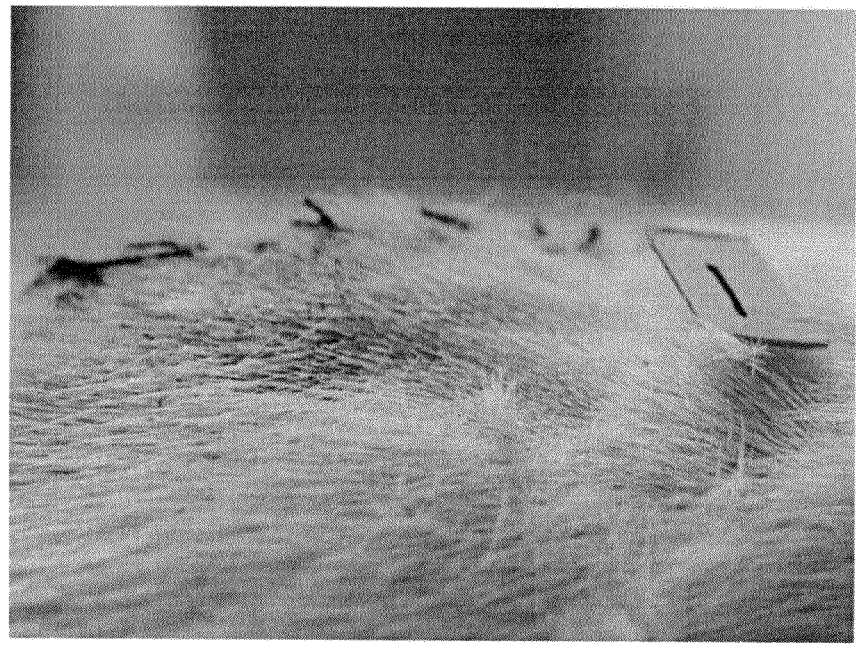
FIG. 11 shows a lateral, external view of a wound site treated with a filament in accordance with the invention on day 14.
Figure 12:
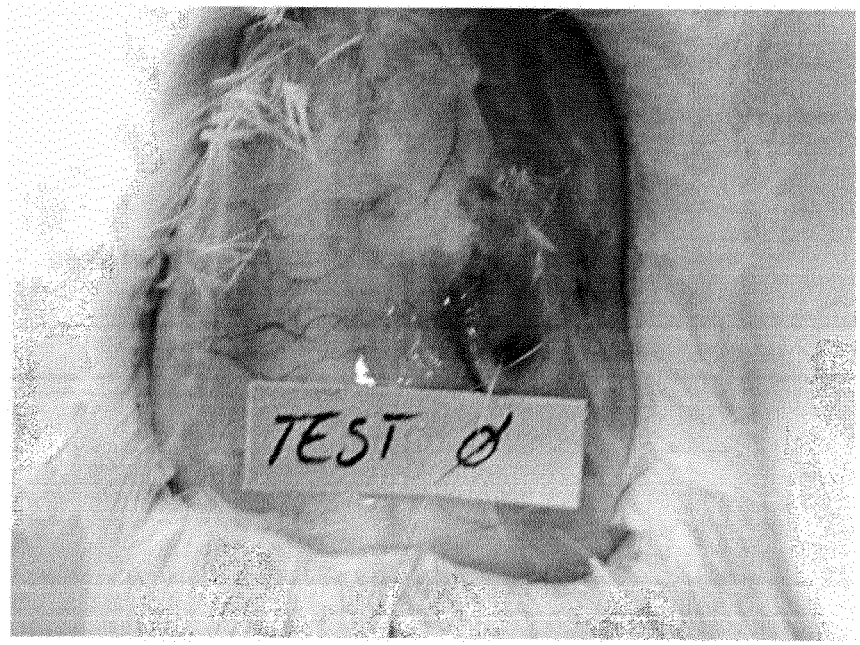
FIG. 12 shows a dorsal, internal view of the site of FIG. 11, showing reduced swelling and reduced pus formation within the paraspinous muscle on day 14.

The use of a test filament with bacteriophages attached is shown in FIG. 11. This was a well healed incision site with minimal swelling on day 14. The internal site exhibited reduced swelling to the wound site and reduced pus formation within the paraspinous muscle on day 14.

Example 7

Immobilisation of Bacteriophages onto Tomato Seeds

Bacteriophage Preparation

We grew *Pectobacterium carotovorum* strains on 20% tryptic soy broth (other suitable medium are also known) and infected the culture with a lytic bacteriophage in the logarithmic phase of growth. When lysis had occurred we purified the bacteriophages by centrifugation and washed the bacteriophage pellet three times by re-suspending in distilled water and concentrating by centrifugation.

Corona Treatment

Tomato seeds were treated with a corona field at 75 kV for 1 second, then immersed in the bacteriophage suspension (an alternative is to spray the treated seeds with the bacteriophage suspension). We washed the seeds with water three times to remove unbound bacteriophages (an alternative is that the bacteriophage suspension be applied to the seeds prior to corona treatment). Note that other field strengths are also effective and washing is only needed to demonstrate that the observed anti-bacterial effects are produced by covalently bound bacteriophages rather than adsorbed "free" bacteriophages.

Germination

We thus prepared seeds that were (i) untreated, (ii) treated with corona discharge, (iii) treated with corona discharge in the presence of bacteriophage and (iv) treated with free bacteriophage, and germinated the seeds on paper moistened with water in a dish at room temperature (an alternative it to germinate on tryptic soy agar (broth with 2% agar) with and without *Pectobacterium*).

Results

Figure 13:
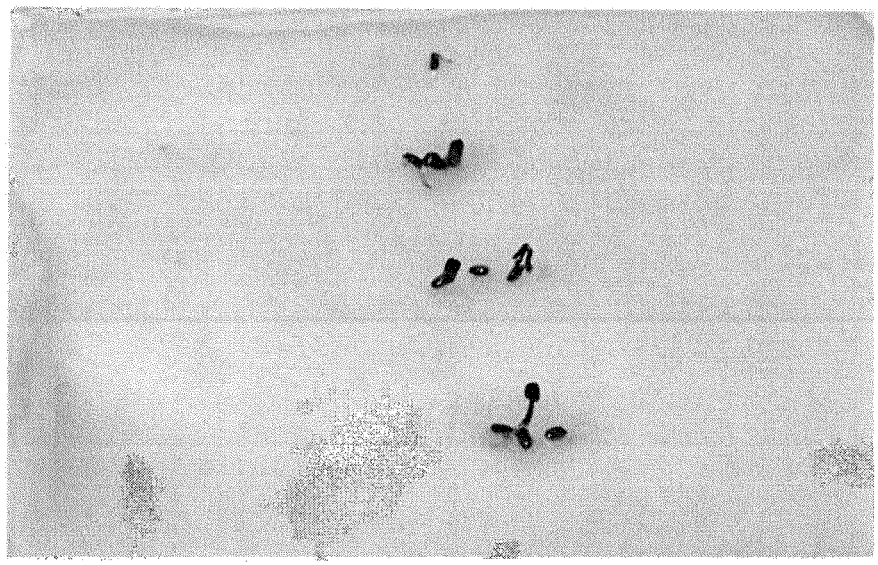
FIG. 13 shows germinated tomato seeds (control)
Figure 14:
FIG. 14 shows germinated tomato seeds with phage immobilised on the seed surfaces in accordance with the invention.
Figure 15:
FIG. 15 shows germinated tomato seeds treated with corona discharge (but no phage)
Figure 16:
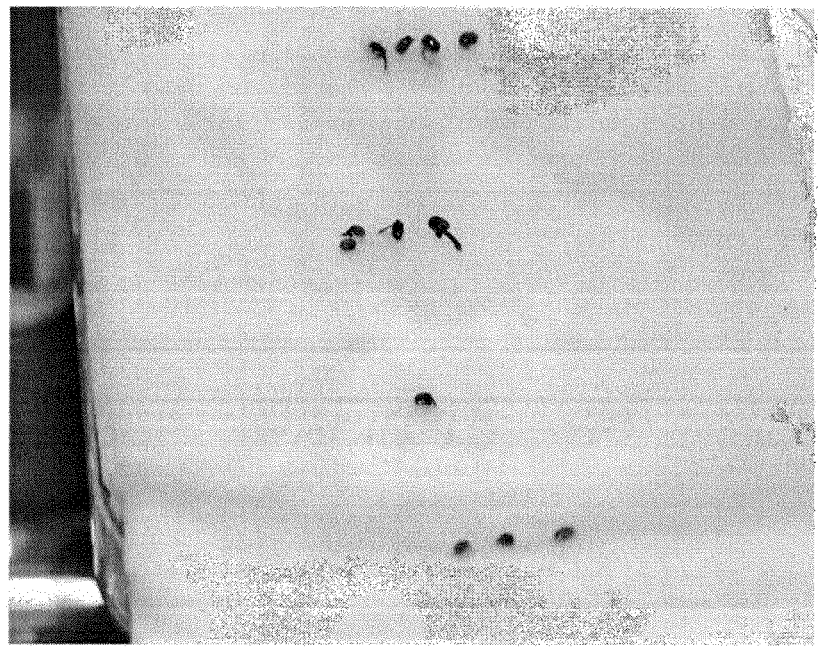
FIG. 16 shows germinated tomato seeds treated with free phage.

Tomato seeds showed enhanced germination with corona (FIG. 15) and corona with anti-*Pectobacterium* phages (FIG. 14) compared with the control (FIG. 13, no corona) and with no phage (FIG. 16). Clearing zones will be seen around the seeds treated with corona and anti-*Pectobacterium* phages on agar inoculated with suitable *Pectobacterium* strains (susceptible to the bacteriophages used). Tomato seed surface is largely cellulose and we then separately tested the viability of bacteriophage immobilised onto cellulose particles—see below.

Example 8

In Vivo Plant Pathogen Assay

We immobilised *Pectobacterium* phages onto cellulose powder (size range approximately 100 microns-1 mm) following the corona discharge methods of WO2007/072049.

We inoculated an agar plate with suitable *Pectobacterium* strains (susceptible to the bacteriophages used) and added treated cellulose particles in three locations.

Figure 17:
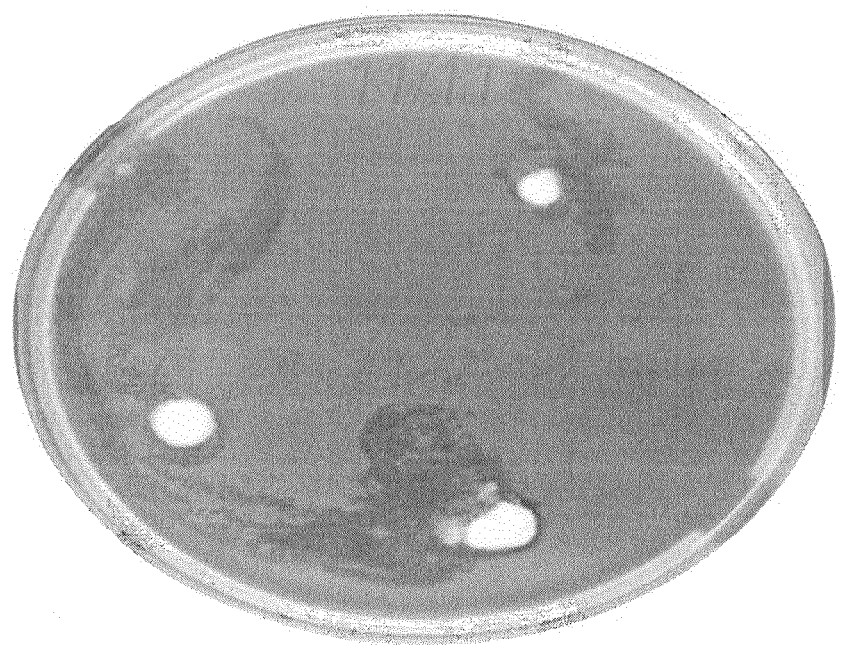
FIG. 17 shows clearing of bacteria around cellulose particles in accordance with the invention.

Referring to the results shown in FIG. 17, clearing around the powder particles can be seen showing the activity against the soft rot bacteria of the immobilised bacteriophages. This confirmed viable bacteriophage were attached to the cellulose material.

Example 9

Bacteriophage on Cellulose Particles

We immobilised *Pectobacterium* phages onto cellulose powder (size range approximately 100 microns-1 mm) following the corona discharge methods of WO2007/072049.

We inoculated agar plates with suitable *Pectobacterium* strains (susceptible to the bacteriophages used) and added treated cellulose particles in three locations.

We treated plates with (i) nothing=control, (ii) free phage in solution and (iii) phage attached to the cellulose particles in solution, and titrated (ii) and (iii) until similar activity in clearing bacteria was observed. Similar activity occurred when approximately 100 free phage were used compared with 1 phage attached to a cellulose particle. This confirmed improved properties of immobilised phage compared with free phage.

Example 10

Treatment of Potatoes

Potato tubers were treated with (i) sterile water=control, (ii) free phage, and (iii) phage specific for the bacterium responsible for potato "blackleg" immobilised onto cellulose particles as per examples 8 and 9. Tubers were sprayed with solution and allowed to dry.

Tubers were planted and growth was recorded as number of plants, total number of stems, and number of plants infected with Blackleg. The results are shown in Table 4.

Hence, we found that treating with *Pectobacterium* and spraying with water (+ve control) had the lowest number of emerging plants and stems with greater incidence of blackleg, comparing to the other treatments.

The treatment with free phage had little effect on the total number of emerged plants.

There was an increase in the number of stems per plant when compared to the +ve control.

Only one plant treatment with free phage had symptoms of blackleg.

The treatment with immobilised phage increased the number of stems per plant when compared to the control, as well as the number of plants emerged. At the last observations, 8 weeks after planting, no symptoms of blackleg had been observed in the tubers treated with immobilised phage, showing persistence of the anti-bacterial activity.

TABLE 1A

Visual results from wounds treated with untreated LVCC or untreated LVCC infected with 100 μl $10^8$ cfu/ml E15 suspended in 5% hog gastric mucin
Untreated sutures

| No. of animals | Procedure | Visual observations |
|---|---|---|
| 3 | Incision only (negative control) | No swelling or inflammation. Slightly raised appearance with presence of clear fluid internally |
| 4 | Incision infected with 100 μl $10^7$ cfu/ml E15 & hog gastric mucin (positive control) | Significantly raised hard lump with presence of dark thick necrotic pus internally |

TABLE 1B

Visual results from wounds treated with either untreated or bacteriophage-treated LVCC & 100 μl of $5 \times 10^7$ cfu/ml E15 suspended in 5% hog gastric mucin

| No. of animals | Appearance of wound | Internal observation |
|---|---|---|
| Untreated sutures | | |
| 10 | Large, hard swollen lump | Dark, pus formation |
| Bacteriophage-treated LVCC | | |
| 10 | Small, raised, swelling | Clear, fluid-filled incision site |

TABLE 2

(Phage activity (P) indicated by clear broth. Bacterial growth (+) by cloudy broth)

| | Exposed strips | | | Shielded strips | | |
|---|---|---|---|---|---|---|
| UV (min) | r1 | r2 | r3 | r1 | r2 | r3 |
| 5 | P | P | P | P | P | P |
| 15 | P | P | P | P | P | P |
| 30 | P | P | P | P | P | P |

TABLE 3

Visual results from wounds treated with either untreated or bacteriophage-treated filaments

| No. of animals | Appearance of wound | Internal observation |
|---|---|---|
| Untreated filaments | | |
| 10 | Large, hard swollen lump | Dark, pus formation |
| Bacteriophage treated filaments | | |
| 10 | Small, raised, swelling | Clear, fluid-filled incision site |

TABLE 4

| Group | No. of plants | No. of stems | No infected with Blackleg |
|---|---|---|---|
| Control | 20 | 52 | 3 |
| Free Phage | 21 | 82 | 1 |
| Immobilised Phage | 26 | 110 | 0 |

The invention claimed is:

1. Plant material, selected from seeds, roots and tubers, to which bacteriophage has been covalently attached, wherein the bacteriophage is attached to the plant material by electrical activation of the plant material and then attaching the bacteriophage to the activated plant material, and wherein the bacteriophage retains infectivity.

2. The plant material of claim 1, being seeds for consumption or seed stock.

3. The plant material of claim 1, being tomato seeds.

4. The plant material of claim 1, for prevention or treatment of a plant disease.

5. The plant material of claim 1, for prevention or treatment of bacterial infections in the gastrointestinal tract.

6. The plant material of claim 1, wherein the bacteriophage is covalently attached to a particle and the particle is covalently attached to the plant material.

7. A method of treating plant material selected from seeds, roots and tubers, comprising activating the plant material and then covalently attaching the bacteriophage to the activated plant material, wherein the bacteriophage retains infectivity.

8. The method of claim 7, wherein the plant material comprises seeds for consumption or seed stock.

9. The method of claim 7, wherein the plant material is for prevention or treatment of a plant disease.

10. The method of claim 7, comprising covalently attaching the bacteriophage to a particle or particles and covalently attaching the particle or particles to the plant material.

11. A composition comprising the plant material of claim 1.

* * * * *

UNITED STATES PATENT AND TRADEMARK OFFICE
CERTIFICATE OF CORRECTION

| | | |
|---|---|---|
| PATENT NO. | : 9,539,343 B2 | Page 1 of 1 |
| APPLICATION NO. | : 14/127429 | |
| DATED | : January 10, 2017 | |
| INVENTOR(S) | : James Chadwick and Michael Mattey | |

It is certified that error appears in the above-identified patent and that said Letters Patent is hereby corrected as shown below:

In the Claims

Column 20, Lines 7-10, should read:
roots and tubers, comprising electrical activation of the plant material and covalent attachment of the bacteriophage to the activated plant material, wherein the bacteriophage retains infectivity.

Signed and Sealed this
Eighteenth Day of April, 2017

Michelle K. Lee
*Director of the United States Patent and Trademark Office*